United States Patent [19]
Wong

[11] 3,958,944
[45] May 25, 1976

[54] VIAL ASSEMBLY

[76] Inventor: Johnson N. S. Wong, 1021 Ashbridge Lane, Harbor City, Calif. 90710

[22] Filed: July 15, 1974

[21] Appl. No.: 488,384

[52] U.S. Cl. ............................. 23/259; 23/292; 215/227
[51] Int. Cl.² ......................................... B01L 3/14
[58] Field of Search ............... 23/253 R, 259, 292; 233/2, 26; 128/2 F; 215/227

[56] References Cited
UNITED STATES PATENTS

| | | | |
|---|---|---|---|
| 3,477,822 | 11/1969 | Hamilton | 23/253 R |
| 3,615,222 | 10/1971 | Mead | 23/253 R X |
| 3,721,528 | 3/1973 | Mead et al. | 23/253 R X |

*Primary Examiner*—Morris O. Wolk
*Assistant Examiner*—Timothy W. Hagan
*Attorney, Agent, or Firm*—Nilsson, Robbins, Dalgarn & Berliner

[57] ABSTRACT

A vial assembly useful in conducting tests which involve charcoal adsorption from fluid and centrifugal separation thereof, and which is particularly useful in radioimmunoassay. The assembly includes a vial, a cap therefor and activated charcoal in the cap. The cap defines a compartment in communication with, but spaced from the open end of the vial. The activated charcoal is releasably secured in the compartment to the cap by means of an asperate inner surface and/or plural spaced protrusions within the cap compartment.

4 Claims, 11 Drawing Figures

VIAL ASSEMBLY

FIELD OF THE INVENTION

The fields of art to which the invention pertains include the fields of charcoal adsorption and centrifuge tubes.

BACKGROUND AND SUMMARY OF THE INVENTION

The present vial assembly is generally useful in any analytical test in which activated charcoal is added to a fluid to adsorb a component thereof and is then centrifugally separated from the fluid. The assembly is particularly useful in the technique known as radioimmunoassay wherein an antigen tagged with a radioisotope (e.g. iodine-125, tritium or carbon-14) is added to a vial together with an antibody and a patient's serum containing a competitive antigen. The tagged antigen and patient's antigen will compete for sites on the antibody so that the more antigen of interest there is in the patient's serum, the less radioactive antigen will be bound to the antibody. By adsorbing and separating the unbound antigen, one can measure the radioactivity of the bound antigen to determine the amount of antigen of interest in the patient's serum.

In conducting such tests, the usual procedure is to add to the mixture of serum, antibody and antigen a quantity of specially treated activated charcoal to selectively adsorb unbound antigen. Thereafter, the vial is placed in a centrifuge to concentrate the charcoal at the bottom thereof and an aliquot portion of the remaining fluid is drawn off by pipette or by decanting for measurement of its radioactivity. To facilitate such tests, kits have been provided in which a three component system is used. A pellet of treated charcoal is bonded to the bottom of a first tube while test solution is contained in a capped second tube. After adding serum to the test solution and incubating, the tubes are connected together and shaken whereby the charcoal mixes with the serum mixture and adsorbs unbound antigen. Thereafter, the charcoal is centrifuged back into the first tube and the assembly is carefully tilted to decant the fluid into the second tube. The first tube is discarded and a radioactivity measurement is made on the second tube.

The present invention provides an improved vial assembly which eliminates one of the foregoing tubes and which also eliminates the need for careful handling during decanting. In particular, the present vial assembly consists of an elongate vial open at one end, a cap therefor and treated charcoal in the cap. The cap is formed internally with retention means so as to successively secure, release and secure the charcoal within a compartment defined by the walls of the cap. In one embodiment, the cap is formed with an asperate inner surface to receive and retain the charcoal. In another embodiment, the cap is formed internally with plural protrusions into the cap compartment to retain the charcoal.

In operation, a serum-antigen-antibody mixture is placed in the vial which is then incubated. The cap is then placed on the vial and the assembly is inverted and shaken to mix the contents. The cap vial is then placed inverted in a centrifuge to concentrate the charcoal back into the cap compartment where it is secured by one or both of the above retention means. The assembly can then be simply turned back upright, without any requirement for great care in doing so. The cap (containing the secured charcoal) is then removed and a radioassay determination is made on the fluid remaining in the vial.

DETAILED DESCRIPTION

Figure 1:
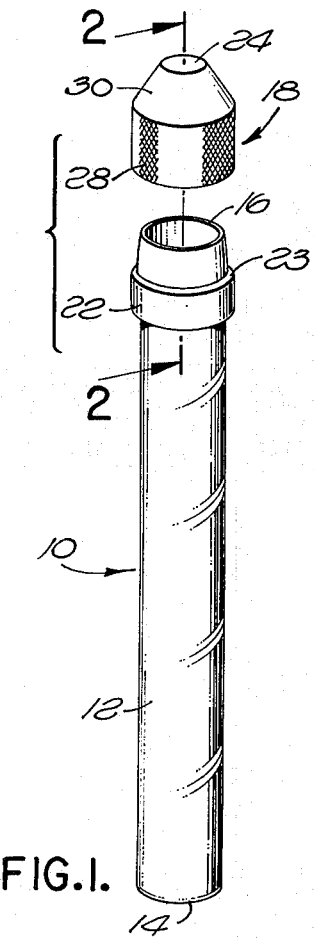
FIG. 1 is a partially exploded, perspective view of a vial-cap assembly of this invention.
Figure 2:
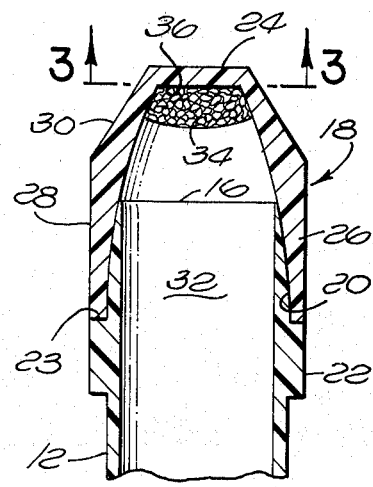
FIG. 2 is a cross-sectional on the line 2—2 of FIG. 1, in the direction of the arrows but with the vial cap connected.

Referring to FIGS. 1 and 2, the assembly includes a vial 10 in the form of an elongate hollow cylindrical tube 12 having a closed bottom end 14 and an open top end 16, and a cap 18 formed with a hollow cylindrical neck section 20 closely fitting over the vial open end 16. The tube and cap are made of thermoplastic (polypropylene, polyethylene or polystyrene) or the like material and are formed so that they have substantially the same internal diameter at their juncture. The tube 12 includes at its top end a cylindrical flange or collar 22 of minor extent spaced downwardly from the open end 16 and which defines an upper annular lip surface 23 for abutment with the mating annular lip surface of the cap neck section 20.

The cap 18 includes an end wall 24 and a cup-shaped side wall 26. The side wall 26 is shaped externally to form the above-mentioned neck section 20, a central externally cylindrical section 28 and frusto-conical section 30. The central section 28 has the largest external diameter and substantially corresponds to the outer diameter of the collar 22 so that a uniform cylindrical outer surface is presented when the cap 18 and vial 10 are connected. Additionally, the outer surface of the central cap section 28 is knurled to provide for better grip.

Internally, the end wall 24 of the cap 18 is sufficiently distant from the open vial end 16 to define a compartment in which is contained a quantity of material spaced from the open vial end 16. The material 34 is in the form of a pellet of fine particles securely bound to the end wall 24.

The material 34 is treated activated charcoal which serves as an adsorbant for radioimmunoassay tests or the like as described above. More specifically, the material comprises a major portion of activated charcoal having sufficient porosity to adsorb unbound antigen but which is sufficiently limited in porosity as to not adsorb antibody-antigen complex. Such treated charcoal is well known to the art and can be prepared, for example, by adding 10 grams of activated charcoal to 100 milliliters of a 2 weight percent solution of dextran, hemoglobin powder, or the like, in water. An aliquot portion of 0.1 ml. is dispensed into the cap 18 to evaporate therein, depositing the pelletized charcoal on the end wall 24.

Figure 3:
FIG. 3 is a partially cross-sectional, partially plan view of the inner terminal wall of the cap depicted in FIG. 2, taken on line 3—3 of FIG. 2, in the direction of the arrows.

In accordance with the present invention, the cap 18 is formed internally with retention means for successively securing, releasing and again securing the material 34 within the compartment 32. Referring additionally to FIG. 3, in one embodiment of the invention, such retention is obtained by providing the end wall 24 with an asperate surface 36, i.e., a surface defined by a plurality of small divisions so as to have a stippled, gridded, reticulated, particulated, grained or otherwise rough or unsmooth texture. Such a surface can be obtained by correspondingly patterning the surface of the mold from which the vial is produced, by mechanical abrasion, by solvent etching, or by any other suitable technique. It will be appreciated that the asperate surface 36 acts to retain the material 34 by providing "tooth" therefor.

Figure 4:
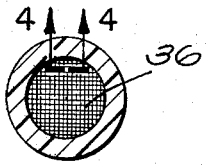
FIG. 4 is a cross-sectional view taken on line 4—4 of FIG. 3, in the direction of the arrows.

Referring to FIG. 4, the particular asperate surface 36 of FIG. 3 is illustrated in magnification and is defined as a grid by a plurality of stipples 38 obtained as a result of embossing depressions into the surface 36 from a patterned mold. The distance between the stipples, as indicated at 40, is about 100–1000 microns, and the widths of the individual stipples are in about the same range.

Figure 5:
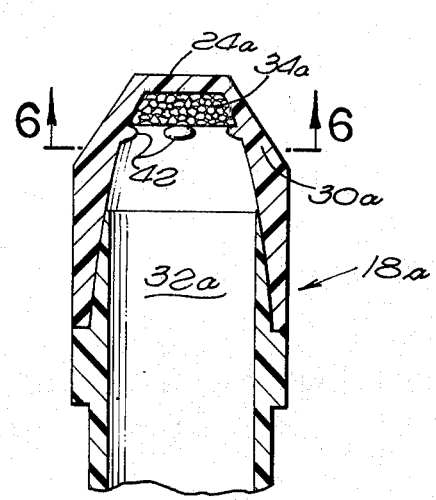
FIG. 5 is a cross-sectional view, similar in view to FIG. 2, but of a second embodiment showing a cap having an alternative internal surface structure.
Figure 6:
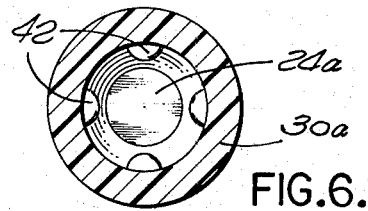
FIG. 6 is a partially cross-section, partially plan view of the internal terminal region of the cap depicted in FIG. 5, taken on line 6—6 of FIG. 5, in the direction of the arrows but omitting charcoal material therefrom for clarity of illustration.

Referring to FIGS. 5 and 6, there is illustrated alternative means for securing the charcoal material 34a. In this embodiment, the cap 18a is generally formed in the same configuration as the cap 18 of FIGS. 1–4, but in place of the grid structure 36, the internal surface of the cup-shaped side wall 30a is formed with a plurality of protrusions into the cap compartment 32a in the form of spaced flaps or nibs 42 annularly around the inner surface of the side wall 30a and spaced downwardly from the end wall 24a. The flaps 42 act as physical barriers to retain the charcoal material. It will be appreciated that in addition to the flaps 42, the inner surface of the end wall 24 can be provided with an asperate texture such as illustrated in FIGS. 3 and 4.

Figure 7:
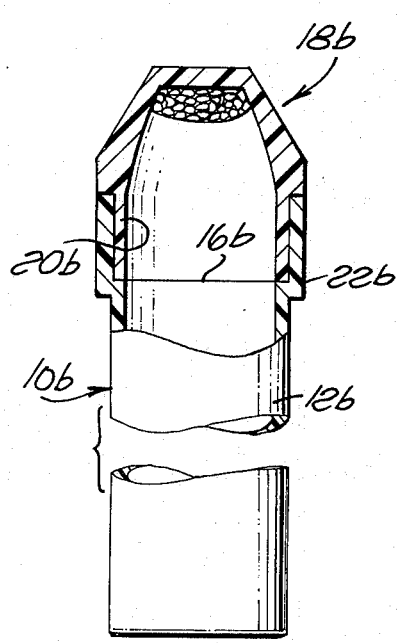
FIG. 7 is a cross-sectional view, similar in view to FIG. 2, but of a third embodiment showing a cap and vial having an alternative mating lip structure.

Referring to FIG. 7, still another alternative embodiment is shown wherein a cap 18b and vial 10b are provided, which are similar to the cap 18 and vial 10 of FIGS. 1 and 2 but with an opposite mating lip structure wherein the neck section 20b of the cap 18b fits within the open end of the vial tube 12b. In this embodiment, the tube 12b is formed with a collar 22b adjacent the top edge of the tube 12b and defining the open vial end 16b as a region of increased internal diameter corresponding to the outer diameter of the cap neck section 20b. As in the embodiment of FIGS. 1 and 2, the components are sized so that uniform cylindrical inner & outer surfaces are presented when the cap 18b and vial 10b are connected.

Figure 8A:
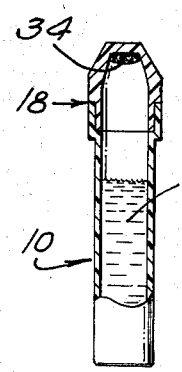
FIGS. 8a–8d are partially cross-sectional views showing the vial assembly of FIG. 1 in various stages of usage.
Figure 8B:
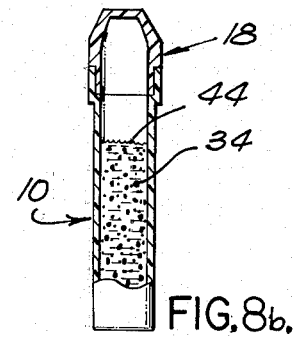
Figure 8C:
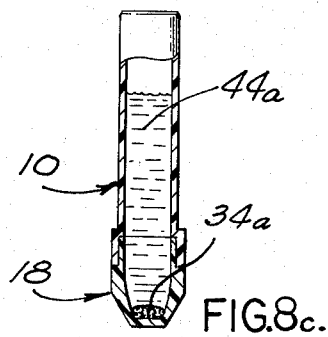
Figure 8D:
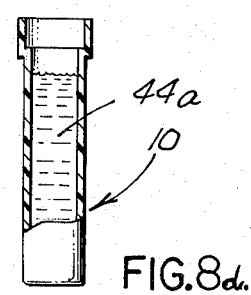

Referring to FIGS. 8a–8d, there is illustrated the manner of use of the present vial assembly. A serum-antibody-antigen (SAA) mixture as above described is placed in the vial 10. Referring to FIG. 8a, following incubation of the SAA mixture 44 for the usual time and temperature for the test being run (as would be known to the art), the cap 18 is placed on the vial and the vial assembly is shaken to release the treated charcoal 34 into the SAA mixture 44 as shown in FIG. 8b. Adsorption starts as soon as the treated charcoal comes into contact with the SAA mixture and unbound antigen is adsorbed by the treated charcoal 34. The vial assembly is then inverted and placed inverted into a centrifuge whereupon the treated charcoal is displaced from the resultant SAA mixture 44a by centrifugal force. Because of the retention surface 36 of FIGS. 3 and 4 (and/or flaps 42 if the cap 18 of FIGS. 5 and 6 is used), the treated charcoal 34a (containing antigen) is again securely bound to the cap end wall 24. Thereafter, the vial assembly need simply be reverted and the cap removed as in FIG. 8d. The vial 10 now contains only the SAA mixture 44a containing antibody-antigen complex with no unbound antigen. Accordingly, the radioactivity of the SAA mixture 44a can be measured to inversely indicate the amount of natural antigen present in the patient's serum. Importantly, reversion of the vial 10 is accomplished without decanting and without any extraordinary care being exercised to prevent dislodgement of the charcoal material 34a which is securely bound to the end wall 24.

I claim:
1. A vial assembly, comprising:
an elongate cylindrical vial open at one end;
a cap for said vial closely but removably fitted on said one end, said cap having a top wall spaced from the open end of said vial and a dependant cylindrical side wall defining a compartment in communication with the interior of said vial, said cap and vial having substantially equal inner diameters at their junction; and
material comprising a major portion of activated charcoal;
said dependent cylindrical cap wall being formed with plural protrusions into said compartment spaced substantially equidistant from said top wall to constitute retention means for successively securing, releasing and again securing said material within said cap compartment against the inner surface of said top wall and spaced from the open end of said vial.

2. The assembly of claim 1 wherein said top wall is formed with an asperate inner surface to constitute additional retention means.

3. The assembly of claim 1 wherein said plural protrusions are spaced substantially equidistant from the open end of said vial.

4. The assembly of claim 1 wherein said cap and at least a top portion of said vial are formed with substantially equal outer diameters at their juncture.

* * * * *